United States Patent
Hwang et al.

(10) Patent No.: US 9,669,066 B2
(45) Date of Patent: Jun. 6, 2017

(54) USE OF KAEMPFERIA PARVIFLORA WALL. EX. BAKER EXTRACTS OR FLAVONE COMPOUND FOR PREVENTING OR TREATING MUSCLE DISEASES, OR IMPROVING MUSCLE FUNCTION

(71) Applicant: Industry-Academic Cooperation Foundation, YonSei University, Seoul (KR)

(72) Inventors: Jae-Kwan Hwang, Goyang-si (KR); Bo Kyung Sa, Chuncheon-si (KR); Tae Yoon Kim, Jecheon-si (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 0 days.

(21) Appl. No.: 14/542,029

(22) Filed: Nov. 14, 2014

(65) Prior Publication Data

US 2015/0190452 A1    Jul. 9, 2015

Related U.S. Application Data

(63) Continuation of application No. PCT/KR2013/004374, filed on May 16, 2013.

(30) Foreign Application Priority Data

May 16, 2012    (KR) .................... 10-2012-0051776

(51) Int. Cl.
```
A01N 65/00      (2009.01)
A61K 36/906     (2006.01)
A61K 31/35      (2006.01)
A61K 31/352     (2006.01)
```
(52) U.S. Cl.
CPC ............ *A61K 36/906* (2013.01); *A61K 31/35* (2013.01); *A61K 31/352* (2013.01)

(58) Field of Classification Search
CPC ..................................................... A61K 36/00
USPC ......................................................... 424/725
See application file for complete search history.

(56) References Cited

FOREIGN PATENT DOCUMENTS

JP    02009067731 A  *  4/2009
JP    02011236133 A  *  11/2011

OTHER PUBLICATIONS

What Is Sarcopenia?, 1 page, 2015.*
ICD-10-CM Diagnosis Code List, Sarcopenia, available at http://www.icd10data.com/ICD10CM/Codes/M00-M99/M60-M63/M62-/M62.84 (last visited Jan. 23, 2017).

Cao et al., Sarcopenia Is Recognized as an Independent Condition by an International Classification of Disease, Tenth Revision, Clinical Modification (ICD-10-CM) Code, 17 JAMDA 675-77 (Dec. 2016).
Cruz-Jentof,t et al., Sarcopenia: European Consensus on Definition and Diagnosis, 39 Age and Ageing 412-423, Table 1 and Fig. 2 (Apr. 2010).
Patel, et al., Prevalence of Sarcopenia in Community-Dwelling Older People in the UK Using the European Working Group on Sarcopenia in Older People (EWGSOP) Definition: Findings From the Hertfordshire Cohort Study (HCS), 42 Age and Aging 378-84 (Feb. 2013).
Lee, et al., Comparisons of Sarcopenia Defined by IWGS and EWGSOP Criteria Among Older People: Results From the I-Lan Longitudinal Aging Study, 14 JAMDA 528e1-528-e7 (May 13, 2013).
Volpato, et al., Prevalence and Clinical Correlates of Sarcopenia in Community-Dwelling Older People: Application of the EWGSOP Definition and Diagnostic Algorithm, 69 J. Gerontol a Biol. Sci. Med. Sci. 438-446 (Apr. 2013).
Yamada, et al., Prevalence of Sarcopenia in Community-Dwelling Japanese Older Adults, 14 JAMDA 911-15 (Oct. 7, 2013).
Chen, et al., Sarcopenia in Asia: Consensus Report of the Asian Working Group for Sarcopenia, 15 JAMDA 95-101, Fig. 1 & Table 3 (Feb. 2014.
Kwon, et al., Prevalence of Sarcopenia in the Korean Woman Based on the Korean National Health and Nutritional Examination Surveys, 23 J Bone. Metab. 23-26 (Feb. 29, 2016).
Gao, et al., Prevalence of Sarcopenia and Associated Factors in Chinese Community-Dwelling Elderly: Comparison Between Rural and Urban Areas, 16 JAMDA 1003e1-1003e6 (Sep. 15, 2015).
Fielding, et al., Sarcopenia: An Undiagnosed Condition in Older Adults. Current Consensus Definition: Prevalence, Etiology, and Consequences. International Working Group on Sarcopenia, 12 J. Am. Med. Dir. Assoc. 249-56, (May 2011).
Wen, et al., Comparisons of Sarcopenia Prevalence Based on Different Diagnostic Criteria in Chinese Older Adults, 19 J. Nutr. Health Aging 342-47 (Mar. 2015).
Patil, et al., Sarcopenia and Osteopenia Among 70-80-Year-Old Home-Dwelling Finnish Women: Prevalence and Association with Functional Performance, 24 Osteoporos Int. 787-96 (2013).
McLean, et al., Developing Consensus Criteria for Sarcopenia: An Update, 30 J. Bone and Mineral Research 588-92 (Apr. 2015).
Hirani, et al., Sarcopenia Is Associated With Incident Disability, Institutionalization, and Mortality in Community-Dwelling Older Men: The Concord Health and Ageing in Men Project, 16 JAMDA 607-13 (Apr. 24, 2015).

(Continued)

*Primary Examiner* — Michael Meller
(74) *Attorney, Agent, or Firm* — H.C. Park & Associates, PLC (57) ABSTRACT

The present invention relates to a pharmaceutical composition containing *Kaempferia parviflora* Wall. Ex. Baker extracts for treating muscle diseases, and more specifically to a pharmaceutical composition containing, as an active ingredient, *Kaempferia parviflora* Wall. Ex. Baker extracts or flavone compound isolated therefrom for treating muscle diseases or a dietary composition for improving muscle function. *Kaempferia parviflora* Wall. Ex. Baker extracts or flavone compound isolated therefrom according to the present invention reduces protein catabolism in the muscles and increases muscle cell differentiation and anabolism, and is thus effective for preparing pharmaceutical composition for treating muscle diseases and dietary composition for improving muscle function.

2 Claims, 3 Drawing Sheets

(56) References Cited

OTHER PUBLICATIONS

Dam et al., An Evidence-Based Comparison of Operational Criteria for the Presence of Sarcopenia, 69 J. Gerontol a Biol. Sci. Med. Sci. 584-90 (May 2014).

Lau et al., "Prevalence of and Risk Factors for Sarcopenia in Elderly Chinese Men and Women", Journal of Gerontology: Medical Sciences, 2005, vol. 60A, No. 2, pp. 213-216, Gerontological Society of America.

Lee et al., "The role of hormones, cytokines and heat shock proteins during age-related muscle loss", Clinical Nutrition, 2007, vol. 26, pp. 524-534, Elsevier Ltd and European Society for Clinical Nutrition and Metabolism.

Zhao et al., "FoxO3 Coordinately Activates Protein Degradation by the Autophagic/Lysosomal and Proteasomal Pathways in Atrophying Muscle Cells", Cell Matabolism, vol. 6, Dec. 2007, pp. 472-483, Elsevier Inc.

Nader, "Molecular determinants of skeletal muscle mass: getting the "AKT" together", The International Journal of Biochemistry & Cell Biology, vol. 37, 2005, pp. 1985-1996, Elsevier Ltd.

Mascher et al., "Changes in signalling pathways regulating protein synthesis in human muscle in the recovery period after endurance exercise", Acta Physiol, vol. 191, 2007, pp. 67-75, Scandinavian Physiological Society.

Zammit et al., "The Skeletal Muscle Satellite Cell: The Stem Cell That Came in From the Cold", Journal of Histochemistry & Cytochemistry, vol. 54, 2006, pp. 1177-1191, The Histochemical Society, Inc.

Carmeli et al., "The biochemistry of aging muscle", Experimental Gerontology, vol. 37, 2002, pp. 477-489, Elsevier Science Inc.

Sutthanut et al., "Simultaneous identification and quantitation of 11 flavonoid constituents in Kaempferia parviflora by gas chromatography", Journal of Chromatography A, vol. 1143, 2007, pp. 227-233, Elsevier B.V.

Shim et al., "The effect of 4-hydroxypanduratin A on the mitogen-activated protein kinase-dependent activation of matrix metalloproteinase-1 expression in human skin fibroblasts", Journal of Dermatological Science, vol. 53, 2009, pp. 129-134, Japanese Society for Investigative Dermatology, Elsevier Ireland Ltd.

Othman et al., "Vasorelaxant Effects of Ethyl Cinnamate Isolated from Kaempferia galanga on Smooth Muscles of the Rat Aorta", Planta Med, vol. 68, 2002, pp. 655-657, Georg Thieme Verlag Stuttgart, New York.

Chaturapanich et al., "Effects of Kaempferia parviflora extracts on reproductive parameters and spermatic blood flow in male rats", Reproduction, col. 136, 2008, pp. 515-522, Society for Reproduction and Fertility.

Trisomboon et al., "Effect of Daily Treatment with Thai Herb, Kaempferia parviflora, in Hershberger Assay Using Castrated Immnture Rats", Journal of Reproduction and Development, vol. 53, No. 2, 2007, pp. 351-356, Society for Reproduction and Development.

Kang et al., "5,7-Dimethoxyflavone induces melanogenesis in B16F10 melanoma cells through cAMP-dependent signalling", Experimental Dermatology, vol. 20, 2011, pp. 445-447, John Wiley & Sons A/S.

* cited by examiner

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Forward primer for beta-actin

<400> SEQUENCE: 1
agccatgtac gtagccatcc        20

<210> SEQ ID NO 2
<211> LENGTH: 20
<212> TYPE: DNA
<213> ORGANISM: Artificial Sequence
<220> FEATURE:
<223> OTHER INFORMATION: Reverse primer for beta-actin

<400> SEQUENCE: 2
ctctcagctg tggtggtgaa        20

<210> SEQ ID NO 3
<211> LENGTH: 20
<212> TYPE: DNA
<213> ORGANISM: Artificial Sequence
<220> FEATURE:
<223> OTHER INFORMATION: Forward primer for Atrogin-1

<400> SEQUENCE: 3
ccctgagtgg catcgcccaa        20

<210> SEQ ID NO 4
<211> LENGTH: 19
<212> TYPE: DNA
<213> ORGANISM: Artificial Sequence
<220> FEATURE:
<223> OTHER INFORMATION: Reverse primer for Atrogin-1

<400> SEQUENCE: 4
aggtcccgcc catcgctca        19

<210> SEQ ID NO 5
<211> LENGTH: 20
<212> TYPE: DNA
<213> ORGANISM: Artificial Sequence
<220> FEATURE:
<223> OTHER INFORMATION: Forward primer for MuRF1

<400> SEQUENCE: 5
tctactcggc cacaggcgct        20

<210> SEQ ID NO 6
<211> LENGTH: 20
<212> TYPE: DNA
<213> ORGANISM: Artificial Sequence
<220> FEATURE:
<223> OTHER INFORMATION: Reverse primer for MuRF1

<400> SEQUENCE: 6
cttgacagct cccgccgcaa        20

<210> SEQ ID NO 7
<211> LENGTH: 20
<212> TYPE: DNA
<213> ORGANISM: Artificial Sequence

```
<220> FEATURE:
<223> OTHER INFORMATION: Forward primer for Myogenin

<400> SEQUENCE: 7
tgggctgcca caagccagac                                              20

<210> SEQ ID NO 8
<211> LENGTH: 20
<212> TYPE: DNA
<213> ORGANISM: Artificial Sequence
<220> FEATURE:
<223> OTHER INFORMATION: Reverse primer for Myogenin

<400> SEQUENCE: 8
cagcccagcc actggcatca                                              20

<210> SEQ ID NO 9
<211> LENGTH: 20
<212> TYPE: DNA
<213> ORGANISM: Artificial Sequence
<220> FEATURE:
<223> OTHER INFORMATION: Forward primer for MyoD

<400> SEQUENCE: 9
ggatggtgcc cctgggtcct                                              20

<210> SEQ ID NO 10
<211> LENGTH: 20
<212> TYPE: DNA
<213> ORGANISM: Artificial Sequence
<220> FEATURE:
<223> OTHER INFORMATION: Reverse primer for MyoD

<400> SEQUENCE: 10
tggccttcgc tgtgagtcgc                                              20
```

USE OF KAEMPFERIA PARVIFLORA WALL. EX. BAKER EXTRACTS OR FLAVONE COMPOUND FOR PREVENTING OR TREATING MUSCLE DISEASES, OR IMPROVING MUSCLE FUNCTION

CROSS-REFERENCE TO RELATED APPLICATIONS

This application is a continuation of International Patent Application No. PCT/KR2013/004374, filed on May 16, 2013, and claims priority from and the benefit of Korean Patent Application No. 10-2012-0051776, filed on May 16, 2012, each of which is incorporated by reference for all purposes as if fully set forth herein.

SEQUENCE LISTING

This application includes sequence listings filed electronically via the USPTO EFS-WEB server. The entire content of these sequence listings are hereby incorporated by reference into the specification of this application. The sequence listings are identified by the electronically filed ASII (.txt) text files as follows:

| File Name | Date of Creation | Size |
|---|---|---|
| Sequence Listing | Nov. 14, 2014 | 1.79 kilobytes |
| Sequence Listing | Feb. 23, 2015 | 1.90 kilobytes |

BACKGROUND

Field

The present invention relates to the use of an extract of *Kaempferia parviflora* Wall. ex Baker or a flavone compound for preventing or treating muscle diseases, and more specifically to a pharmaceutical composition for treating muscle diseases or a dietary composition for improving muscle function comprising an extract of *Kaempferia parviflora* Wall. ex Baker or a flavone compound as an active ingredient.

DISCUSSION OF THE BACKGROUND

It was reported that approximately 24% of the population between the ages of sixty five and seventy experience age-related muscle atrophy, and 20% of them suffer from the loss of muscle functions (J. Gerontol. A Biol. Sci. Med. Sci. 60(2): 21316, 2005). As the body ages, there is a reduction in the release of hormones involved in anabolism, the process of synthesizing proteins, such as growth hormones, sex hormones, and insulin-like growth factors, and subsequently protein synthesis in the muscles is suppressed. On the other hand, the levels of circulating inflammatory cytokines increase, such as tumor necrosis factor-α (TNF-α), degrading regeneration capacity of muscle fibers. TNF-α can ultimately cause the loss of skeletal muscle tissues by binding to the damaged muscled fibers, suppressing their differentiation, and promoting catabolism which is the process of breaking down proteins in the muscles (Clin. Nutr. 26(5): 52434, 2007).

When the forkhead box (foxo) pathway, a major signaling pathway inducing muscle atrophy, is activated by the age-related chronic inflammation, the expression of E3 ubiquitin ligases involved in protein degradation, such as atrogin-1 and MuRF1, is upregulated (Cell Metab. 6(6): 47283, 2007). On the contrary, PI3K/AKT signaling pathway suppresses the activity of foxo and induces muscle growth by activating a protein synthesis-associated factor, mammalian target of rapamycin (mTOR) (Int. J. Biochem. Cell Biol. 37(10): 1985-96, 2005). Notably, PI3K/AKT and mTOR are exercise-induced signals participating in the enhancement of exercise performance by increasing muscle mass (Acta. Physiol (Oxf). 191(1): 67-75, 2007).

Differentiation of muscle cells is regulated by diverse muscle regulatory factors (MRFs) such as myoD, myf5, myogenin, and mrf4. MyoD initiates the muscle-specific gene expression and induces differentiation of the mesenchymal cells into muscle cells. Further, myoD regulates induction of myogenin expression. Accordingly, the regeneration of damaged muscle cells can treat or prevent muscle atrophy caused by aging or chronic inflammation (J. Histochem. Cytochem. 54(11): 1177-91, 2006).

Not only age-associated muscle atrophy is a matter of the muscle function itself, but also it is closely related to osteoporosis, progression into numerous diseases, and injuries from a fall. Therefore, it is critical to treat age-associated muscle atrophy at the earliest possible time with right exercise and nutritional regimen (Exp. Gerontol. 37(4): 477-89, 2002).

SUMMARY

The present inventors have conducted the investigation on natural materials that can regulate muscle functions. As a result, the present inventors found that an extract of *Kaempferia parviflora* Wall. ex Baker or a flavone compound therefrom has effects in reducing protein catabolism in the muscles and promotes muscle cell differentiation and protein anabolism, thereby completing the present invention.

Accordingly, it is an object of the present invention to provide a pharmaceutical composition for preventing or treating muscle diseases comprising an extract of *Kaempferia parviflora* as an active ingredient.

Another object of the present invention is to provide a pharmaceutical composition for preventing or treating muscle diseases comprising a compound represented by the following Formula 4 or salt thereof as an active ingredient.

[Formula 4]

In Formula 4, each of $R_1$, $R_2$, and $R_3$ independently denotes hydrogen or methoxy.

Still another object of the present invention is to provide a dietary composition for improving muscle functions or enhancing exercise performance comprising an extract of *Kaempferia parviflora* as an active ingredient.

Still another object of the present invention is to provide a dietary composition for improving muscle functions or enhancing exercise performance comprising a compound represented by Formula 4 or salt thereof as an active ingredient.

To achieve the above object, the present invention provides a pharmaceutical composition for preventing or treating muscle diseases comprising an extract of *Kaempferia parviflora* as an active ingredient.

To achieve another object, the present invention provides a pharmaceutical composition for preventing or treating muscle diseases comprising a compound represented by Formula 4 or salt thereof as an active ingredient.

To achieve still another object, the present invention provides a dietary composition for improving muscle functions or enhancing exercise performance comprising an extract of *Kaempferia parviflora* as an active ingredient.

To achieve still another object, the present invention provides a dietary composition for improving muscle functions or enhancing exercise performance comprising a compound represented by Formula 4 or salt thereof as an active ingredient.

Hereafter, the present invention is described in detail.

The present invention provides a pharmaceutical composition for preventing or treating muscle diseases comprising an extract of *Kaempferia parviflora* as an active ingredient.

The *Kaempferia parviflora* extract of the present invention may be an extract from rhizome, although not limited thereto.

*Kaempferia parviflora*, a plant belonging to the Zingiberaceae family, is also called black ginger.

The *Kaempferia parviflora* extract of the present invention can be prepared by the methods of extracting natural materials well-known in the art, and preferably may be extracted using one or more solvents selected from the group consisting of distilled water, an organic solvent having one to six carbon atoms, and supercritical fluids, and more preferably, the extraction solvent may be an aqueous solution of an alcohol having one to six carbon atoms. The above-mentioned organic solvent having one to six carbon atoms may be selected from the group consisting of alcohol, acetone, ether, benzene, chloroform, ethyl acetate, methylene chloride, hexane, cyclohexane, and petroleum ether, each of which has one to six carbon atoms.

In addition, the *Kaempferia parviflora* extract of the present invention may be prepared by isolating and purifying rhizome of dry *Kaempferia parviflora* using distilled water acceptable for food processing, ethanol, subcritical water, or supercritical carbon dioxide, or from oil obtained by pressing *Kaempferia parviflora*.

The present invention provides a pharmaceutical composition for preventing or treating muscle diseases comprising a compound represented by Formula 4 or salt thereof as an active ingredient.

Preferably a compound represented by Formula 4 may be selected from the group consisting of 5,7-dimethoxyflavone, 5,7,4'-trimethoxyflavone, and 3,5,7,3'4'-pentamethoxyflavone.

All of the 5,7-dimethoxyflavone, 5,7,4'-trimethoxyflavone, and 3,5,7,3'4'-pentamethoxyflavone belong to flavone compounds.

The above-mentioned 5,7-dimethoxyflavone, 5,7,4'-trimethoxyflavone, and 3,5,7,3'4'-pentamethoxyflavone of the composition of the present invention may be produced by chemical synthesis, or isolated and purified from *Kaempferia parviflora* or other plants.

The flavone compound of the present invention may be used as it is or in the form of a pharmaceutically acceptable salt. As used herein, the phrase "pharmaceutically acceptable" means that the components present in the composition are physiologically acceptable and usually do not invoke allergic or similar reactions when administered to humans. Specifically, the salt may be an acid addition salt formed from a pharmaceutically acceptable free acid. The free acid may be an organic or inorganic acid. The organic acid includes but is not limited to citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, glutamic acid and aspartic acid. And, the inorganic acid includes but is not limited to hydrochloric acid, bromic acid, sulfuric acid and phosphoric acid.

*Kaempferia parviflora* is a plant belonging to the Zingiberaceae family, and also called black ginger. The *Kaempferia parviflora* extract of the present invention contains a large amount of flavone compounds, specifically 5,7-dimethoxyflavone, 5,7,4'-trimethoxyflavone, and 3,5,7,3'4'-pentamethoxyflavone.

For isolation and purification of the flavone compound of the present invention from the extract of *Kaempferia parviflora*, column chromatography or high-performance liquid chromatography (HPLC) using silica gel, activated alumina or various other synthetic resins may be used alone or in combination, although not limited thereto.

The present inventors confirmed that the extract of *Kaempferia parviflora* or the flavone compound represented by Formula 4 therefrom has the effect of suppressing muscle protein degradation, promoting protein synthesis and muscle cell differentiation, and increasing muscle mass (refer to Experimental example 1 to 3).

Therefore, the extract of *Kaempferia parviflora* or the flavone compound represented by Formula 4 therefrom can be used to treat muscle diseases resulting from muscle wasting or degeneration. Examples of the muscle diseases include atony, muscular atrophy, muscular dystrophy, muscle degeneration, myasthenia, and sarcopenia. Muscle wasting is characterized by progressive loss of muscle mass and weakening and degeneration of muscles, specifically skeletal muscles or voluntary muscles and cardiac muscles. Muscle wasting and degeneration are caused by genetic factors, acquired factors, and aging. The composition of the present invention has the effect of promoting an increase in muscles, which is not limited to the types of muscles. "Increase in muscles" means increasing muscular performance among the components of the body, and muscle mass can be increased by physical exercise and improvement in endurance, and by administering a material having the effect of increasing muscles in the body.

The pharmaceutical composition according to the present invention may comprise the extract of *Kaempferia parviflora* or a compound represented by Formula 4 alone or in combination with one or more pharmaceutically acceptable carrier, excipient or diluent generally used in the preparation of pharmaceutical compositions.

In case of oral administration, the composition of the present invention may be formulated with a proper carrier for oral administration into powders, granules, tablets, pills, and sugar-coated tablets, capsules, liquids, gels, syrups, slurries, and emulsions by using the methods well-known in the art. For examples of appropriate carriers, it may comprise sugars comprising lactose, dextrose, sucrose, sorbitol, mannitol, xylitol, erythritol, and maltitol, starches comprising corn starch, wheat starch, rice starch and potato starch, celluloses comprising cellulose, methyl cellulose, sodium carboxymethylcellulose, and hydroxypropylmethylcellulose, and fillers comprising gelatin and polyvinylpyrrolidone. And, if desired, it may comprise cross-linked polyvinylpyrrolidone, agar, alginic acid or sodium alginate as a disintegrating agent. Further, the inventive pharmaceutical composition may comprise anti-coagulants, lubricants, wetting agents, flavors, emulsifying agents, and antiseptics.

Also, in case of parenteral administration, a pharmaceutical composition of the present invention may be formulated with a proper carrier for parenteral administration into injections, transdermal preparations, and nasal inhalers by using the methods well-known in the art. The injection must be sterilized and protected from microorganisms such as bacteria and fungi. Proper carriers for injection may be, but not limited thereto, water, ethanol, polyol (e.g. glycerol, propylene glycol and liquid polyethylene glycol) or mixture thereof and/or solvent or dispersing media comprising plant oil. More preferably, proper carriers may be Hank's solution, Ringer's solution, PBS (Phosphate buffered saline) containing triethanol amine, or a isotonic solution such as distilled water for injection, 10% ethanol, 40% ethanol, 40% propylene glycol and 5% dextrose.

To protect the injection from contamination of microorganisms, it may further comprise various antibiotics or antifungal reagent such as paraben, chlorobutanol, phenol, sorbic acid, thimerosal. In addition, in most cases, the injection may further comprise an isotonic reagent such as sugars or sodium chloride.

In case of transdermal preparations, it comprises ointments, creams, lotions, gels, topical solutions, plaster, liniments and aerosols. The "transdermal preparations" means administering a pharmaceutical composition partially to the skin and delivering effective amount of an active ingredient through the skin. The formulation of the above-mentioned is well-described in Remington's Pharmaceutical Science, 15th Edition, 1975, Mack Publishing Company, Easton, Pa.

In case of nasal inhalers, a compound of the present invention may be delivered in a form of aerosol spray from a pressure pack or spray by using proper propellants such as dichlorofluoromethane, trichlorofluoromethane, dichlrorotetrafluoroethane, carbon dioxide, or other proper gas. In case of pressure aerosols, dose may be determined by providing a valve which delivers the measured amount of a compound. For example, a gelatin capsule and cartridge for inhaler or insufflator may be formulated to contain the compound, and proper powder compound such as lactose or starch. Other pharmaceutically acceptable carriers are well-described in Remington's Pharmaceutical Sciences, 19th ed., Mack Publishing Company, Easton, Pa., 1995.

Also, a pharmaceutical composition of the present invention may further comprise one or more buffers (e.g. saline or PBS), carbohydrates (e.g. glucose, mannose, sucrose or dextran), antioxidant, bacteriostat, chelating agent (e.g. EDTA or glutathione), adjuvant (e.g. aluminium hydroxide), suspension agent, thickening agent and/or preservative.

The suitable dose of the extract or compound according to the present invention may vary according to the patient's condition, body weight, disease severity, types of formulation, administration routes, and treatment length, but may be properly determined by the skilled person in the related art. But for the treatment to be effective, the compound of the present invention may be administered with the dose of 0.001 to 300 mg/day/kg body weight, and preferably 0.01 to 200 mg/day/kg body weight. However, such pharmaceutically effective dose may be suitably adjusted considering various factors such as types of diseases, disease severity, patient's age, body weight, health condition, sex, administration routes, and treatment length.

As used herein, "pharmaceutically acceptable" means non-toxic composition which is physiologically acceptable and, when administered to human beings, generally does not cause allergic reactions, such as gastrointestinal disorder and dizziness, or similar reactions thereto as well as not inhibiting reaction of an active ingredient. The carrier comprises all kinds of solvents, dispersing media, oil-in-water or water-in-oil emulsions, water soluble compositions, liposomes, microbeads and microsomes.

The composition of the present invention may be administered by various routes to mammals such as rats, mice, livestock, and humans. All possible routes of administration may be applied, for example, oral, intrarectal, intravenous, intramuscular, subcutaneous, intravaginal, intrathecal, or intracerebroventricular injection.

The present invention provides the use of the extract of *Kaempferia parviflora* or a compound represented by Formula 4 or salt thereof for preparing an agent to treat or prevent muscle diseases.

The present invention provides a method for preventing or treating muscle diseases including administering an effective amount of the extract of *Kaempferia parviflora* or a compound represented by Formula 4 or salt thereof to a subject in need thereof.

The extract of *Kaempferia parviflora* or a compound represented by Formula 4 or pharmaceutically acceptable salt thereof of the present invention may be administered by various routes including oral, transdermal, subcutaneous, intravenous or intramuscular administration with an effective amount. As used herein, "effective amount" refers to an amount of a composition or extract which exhibits the effect of preventing or treating muscle diseases when it is administered to the patient. As used herein, "subject" may comprise an animal, particularly a mammal including a human as well as cells, tissues, organs derived from an animal. A subject may refer to a patient in need of treatment thereof.

The extract of *Kaempferia parviflora* or a compound represented by Formula 4 or pharmaceutically acceptable salt thereof of the present invention may be administered as it is or as various types of formulations prepared as described above, preferably until the treatment results in a desired effect of preventing or treating muscle diseases. A compound or pharmaceutically acceptable salt thereof of the present invention may be administered by various routes according to the methods well-known in the art. Administration routes may be oral or parenteral, for example, oral, intramuscular, intravenous, intracutaneous, intraarterial, intraosseous, intrathecal, intraperitoneal, nasal, intravaginal, intrarectal, sublingual, or subcutaneous administration, or through the gastrointestinal tract, mucosal membrane or respiratory tract. For example, the extract or the compound or pharmaceutically acceptable salt thereof of the present invention may be applied topically on the skin or prepared into an injectable formulation, and then administered by lightly pricking the skin with a 30 gauge thin injection needle. Preferably it may be directly applied to the skin of a subject. In addition, a compound or pharmaceutically acceptable salt thereof of the present invention may be administered as attached to the molecules evoking high-affinity binding to the target cells or tissues (for example, skin cells or skin tissue), or as capsulated within such molecules. A compound or pharmaceutically acceptable salt thereof of the present invention can be coupled or cross-liked with sterols (for example, cholesterol), lipids (for example, cationic lipids, virosomes or liposomes) or target cell-specific bonding agents (for example, ligands recognized by target-cell specific receptors) using the methods well-known in the art. Coupling agents or cross-linking agents include, but not limited to, protein A, carbodiimide, N-succinimidyl-3-(2-pyridyldithio) propionate (SPDP).

These formulations are described in Remington's Pharmaceutical Science, 15th Edition, 1975, Mack Publishing Company, Easton, Pa., which is general reference well-known in the pharmaceutical chemistry field.

In addition, the present invention provides a dietary composition for improving muscle functions or enhancing exercise performance comprising an extract of *Kaempferia parviflora* or a compound represented by Formula 4 or salt thereof as an active ingredient.

"Improving muscle functions" means that primary characteristics or functions of muscles are strengthened such as increase in muscle mass, muscular strength, and ability to recover from fatigue. Also, the extract of *Kaempferia parviflora* or the flavone compound of the present invention increases the expression of PI3K/AKT and mTOR (refer to <Experiment 2>), and these factors participate in enhancing exercise performance by increasing muscle mass (Acta. Physiol. (Oxf). 191(1): 67-75, 2007).

The dietary composition of the present invention encompasses all types of food comprising functional foods, nutritional supplements, health food, and food additives. The dietary composition may be prepared into various forms according to the methods well-known in the related art.

For example, the extract of *Kaempferia parviflora* or the compound represented by Formula 4 or salt thereof of the present invention may be prepared in the form of tea, juice or drink for drinking as a health food, or may be formulated into granules, capsules or powder. The *Kaempferia parviflora* extract or the compound represented by Formula 4 or salt thereof of the present invention may be formulated into a composition by mixing with other known active ingredients effective in improving muscle functions.

Also, a functional food may be prepared by adding the extract of *Kaempferia parviflora* or the compound represented by Formula 4 or salt thereof of the present invention to beverages (including alcoholic beverages), fruits, and processed foods thereof (e.g. canned fruits, bottled fruits, jam, marmalade and the like), fishes, meats, and processed foods thereof (e.g. ham, sausages, corn beef), bread and noodles (e.g. Japanese noodles, buckwheat noodles, ramen, spaghetti, macaroni and the like), juices, drinks, cookies, Korean taffy, dairy products (e.g. butter, cheese and the like), eatable plant oils, margarine, plant proteins, retort foods, frozen foods, and various seasonings (e.g. soybean paste, soy sauce, sauce and the like).

Preferably the content of the extract of *Kaempferia parviflora* or the compound represented by Formula 4 or salt thereof in the dietary composition of the present invention may be 0.01 to 100% (w/w) of the final food product, although not limited thereto.

Also, in order to use the extract of *Kaempferia parviflora* or the compound represented by Formula 4 or salt thereof of the present invention as food additives, it may be formulated into powder or concentrate.

As described above, the extract of *Kaempferia parviflora* or the compound represented by Formula 4 or salt thereof of the present invention can be useful in preparing a pharmaceutical composition for treating muscle diseases or a dietary composition for improving muscle functions because it inhibits protein catabolism in the muscles and promote muscle cell differentiation and protein anabolism.

DETAILED DESCRIPTION OF THE ILLUSTRATED EMBODIMENTS

Hereinafter, the present invention will be described in detail with reference to examples. It is to be understood, however, these examples are for illustrative purposes only and are not intended to limit the scope of the present invention.

Example 1

Preparation of the Extract of *Kaempferia parviflora* (Black Ginger) Using Ethanol Dried rhizome of *Kaempferia parviflora* was crushed in a mixer, and 100 g of the crushed *Kaempferia parviflora* sample was stirred in 1 L of ethanol at room temperature for 48 hours for cold extraction. The extracted sample was filtered twice through Whatman No. 2 filter paper, and the filtered extract was concentrated in a vacuum rotary evaporator to remove the solvent to yield 9.56 g of an ethanol extract of *Kaempferia parviflora*.

Example 2

Isolation of the Flavone Compound from the Extract of *Kaempferia parviflora*

<2-1> Isolation and Determination of Structure of 5,7-dimethoxyflavone

The concentrated extract of *Kaempferia parviflora* obtained in Example 1 was loaded into a column packed with 6×15 cm silica gel and was fractionated using a solvent system consisting of ethyl acetate and methanol mixed with each other at a ratio of 10:0.5 (v/v). The concentrated component was divided into a total of five fractions according to the order of fractionation, and each fraction was concentrated and dried. Among the five fractions, No. 3 fraction (fraction 3) was subjected to Rp-18 column chromatography (Lichroprep RP-18 25~40 µm, Merck & Co., USA) using a developing solvent of 70% methanol. The concentrated component was divided into two fractions according to the order of fractionation, and each fraction was concentrated and dried. Among the two fractions, No. 2 fraction (fraction 3-2) was loaded into a column packed with 6×15 cm silica gel and was fractionated using a solvent system consisting of ethyl acetate and methanol mixed with each other at a ratio of 10:0.4 (v/v). Finally, No. 1 fraction among the two (fraction 3-2-1) was concentrated and dried and separated out UV-blocking substances.

In order to determine the structure of the single active substance, the $^1$H-NMR spectrum and $^{13}$C-NMR spectrum of the single active substance were measured at 500 MHz and 125 MHz (solvent: CDCl3), respectively. In the EI/MS, [M] was observed at m/z 282, thus molecular weight of the present compound was found to be 282. The results of the above $^1$H-NMR, $^{13}$C-NMR and EI/MS were analyzed comparatively with a previous study report (Sutthanut K. et al., J. Chromatogr A., 1143: 227-233, 2007). As a result, it was found that the single substance isolated above was 5,7-dimethoxyflavone represented by the following formula

[Formula 1]

<2-2> Isolation and Determination of Structure of 5,7,4'-trimethoxyflavone

The concentrated extract of *Kaempferia parviflora* obtained in Example 1 was loaded into a column packed with 6×15 cm silica gel and was fractionated using a solvent system consisting of ethyl acetate and methanol mixed with each other at a ratio of 10:0.5 (v/v). The concentrated component was divided into a total of five fractions according to the order of fractionation, and each fraction was concentrated and dried. Among the five fractions, No. 4 fraction (fraction 4) was subjected to Rp-18 column chromatography (Lichroprep RP-18 25~40 µm, Merck & Co., USA) using a developing solvent of 70% methanol. The concentrated component was divided into two fractions according to the order of fractionation, and each fraction was concentrated and dried. Finally, No. 2 fraction (fraction 4-2) was concentrated and dried, and separated out UV-blocking substances.

In order to determine the structure of the single active substance, the $^1$H-NMR spectrum and $^{13}$C-NMR spectrum of the single active substance were measured at 500 MHz and 125 MHz (solvent: CDCl3), respectively. In the EI/MS, [M] was observed at m/z 312, thus molecular weight of the present compound was found to be 312. The results of the above $^1$H-NMR, $^{13}$C-NMR and EI/MS were analyzed comparatively with a previous study report (Sutthanut K. et al., J. Chromatogr A., 1143:227-233, 2007). As a result, it was found that the single substance isolated above was 5,7,4'-trimethoxyflavone represented by the following formula 2:

[Formula 2]

<2-3> Isolation and Determination of Structure of 3,5,7,3',4'-pentamethoxyflavone The concentrated extract of *Kaempferia parviflora* obtained in Example 1 was loaded into a column packed with 6×15 cm silica gel and was fractionated using a solvent system consisting of ethyl acetate and methanol mixed with each other at a ratio of 10:0.5 (v/v). The concentrated component was divided into a total of five fractions according to the order of fractionation, and each fraction was concentrated and dried. Among the five fractions, No. 3 fraction (fraction 3) was subjected to Rp-18 column chromatography (Lichroprep RP-18 25~40 µm, Merck & Co., USA) using a developing solvent of 70% methanol. The concentrated component was divided into two fractions according to the order of fractionation, and each fraction was concentrated and dried. Finally, No. 1 fraction (fraction 3-1) was concentrated and dried, and separated out UV-blocking agents.

In order to determine the structure of the single active substance, the $^1$H-NMR spectrum and $^{13}$C-NMR spectrum of the single active substance were measured at 500 MHz and 125 MHz (solvent: CDCl3), respectively. In the EI/MS, [M] was observed at m/z 372, thus molecular weight of the present compound was found to be 372. The results of the above $^1$H-NMR, $^{13}$C-NMR and EI/MS were analyzed comparatively with a previous study report (Sutthanut K. et al., J. Chromatogr A., 1143:227-233, 2007). As a result, it was found that the single substance isolated above was 3,5,7,3',4'-pentamethoxyflavone represented by the following formula 3:

[Formula 3]

Experimental Example 1

Effects of Reducing Protein Catabolism in the Muscles

Muscle cell-line L6 myoblast (American Type Culture Collection, Manassas, Va., USA) was cultured in DMEM (10% FBS, 100 U/mL penicillin, 100 g/mL streptomycin). When the cell density reached approximately 80~85%, differentiation was induced for six days by replacing the culture medium with DMEM growth medium supplemented with 2% FBS for further experiments. In order to evoke muscle reduction in the differentiated L6 cells, cells were treated with TNF-α for 24 hours followed by the treatment with 5,7-dimethoxyflavone prepared in Example 2-1 at different concentrations (1 or 5 µM). RT-PCR experiments were performed to examine the expression levels of atrogin-1 and MuRF1, major ligases involved in protein catabolism in the muscles. Total RNA was obtained from the differentiated cells using Trizol (Invitrogen, Carlsbad, Calif., USA) and subjected to reverse transcription as follows. Total RNA isolated as above was reverse-transcribed using reverse transcriptases. The following primers were used for RT-PCR experiments.

```
β-actin
                                             (SEQ ID NO: 1)
Forward primer: 5'-AGCCATGTACGTAGCCATCC-3'
                                             (SEQ ID NO: 2)
Reverse primer: 5'-CTCTCAGCTGTGGTGGTGAA-3'

Atrogin-1
                                             (SEQ ID NO: 3)
Forward primer: 5'-CCCTGAGTGGCATCGCCCAA-3'
                                             (SEQ ID NO: 4)
Reverse primer: 5'-AGGTCCCGCCCATCGCTCA-3'

MuRF1
                                             (SEQ ID NO: 5)
Forward primer: 5'-TCTACTCGGCCACAGGCGCT-3'
                                             (SEQ ID NO: 6)
Reverse primer: 5'-CTTGACAGCTCCCGCCGCAA-3'
```

Figure 1:
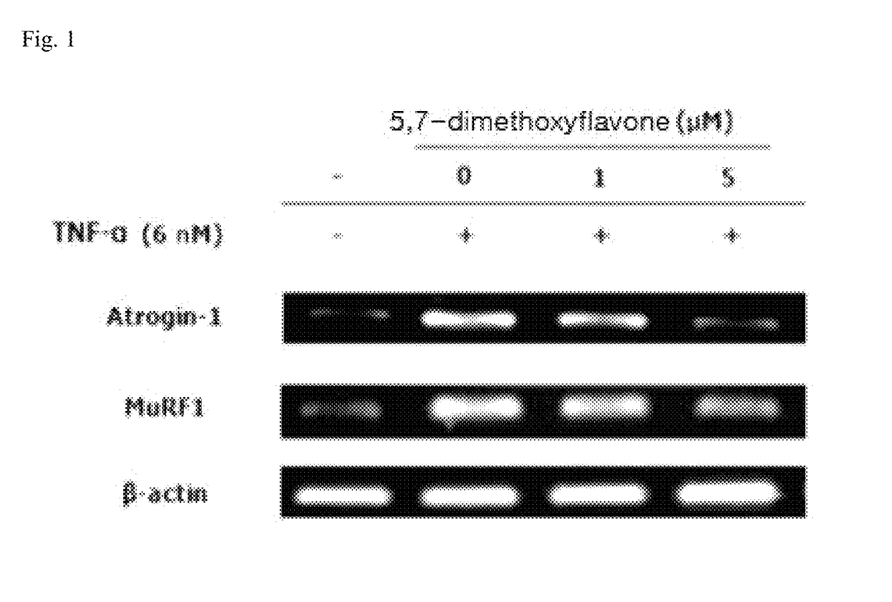
FIG. 1 shows the reduced levels of mRNA expression of atrogin-1 and MuRF1 in muscle cells upon application of 5,7-dimethoxyflavone according to the present invention examined by RT-PCR experiments.

Relative levels of mRNA for each gene was normalized by the value of β-actin. As shown in FIG. 1, 5,7-dimethoxyflavone reduces the mRNA levels of atrogin-1 and MuRF, major ligases involved in protein catabolism in the muscles at the level of gene transcription.

Experimental Example 2

Effects of Increasing Muscle Differentiation and Anabolism

<2-1> Effects of Increasing Muscle Differentiation

In the same manner as Experimental example 1, RT-PCR experiments were performed after total RNA was harvested from the differentiated cells and reverse-transcribed. At this point, RT-PCR was performed with the cells differentiated as described in Experimental example 1 and treated with the extract of *Kaempferia parviflora* (1 or 10 μg/ml) in addition to 5,7-dimethoxyflavone.

```
Myogenin
                                             (SEQ ID NO: 7)
Forward primer: 5'-TGGGCTGCCACAAGCCAGAC-3'
                                             (SEQ ID NO: 8)
Reverse primer: 5'-CAGCCCAGCCACTGGCATCA-3'

MyoD
                                             (SEQ ID NO: 9)
Forward primer: 5'-GGATGGTGCCCCTGGGTCCT-3'
                                             (SEQ ID NO: 10)
Reverse primer: 5'-TGGCCTTCGCTGTGAGTCGC-3'
```

Figure 2:
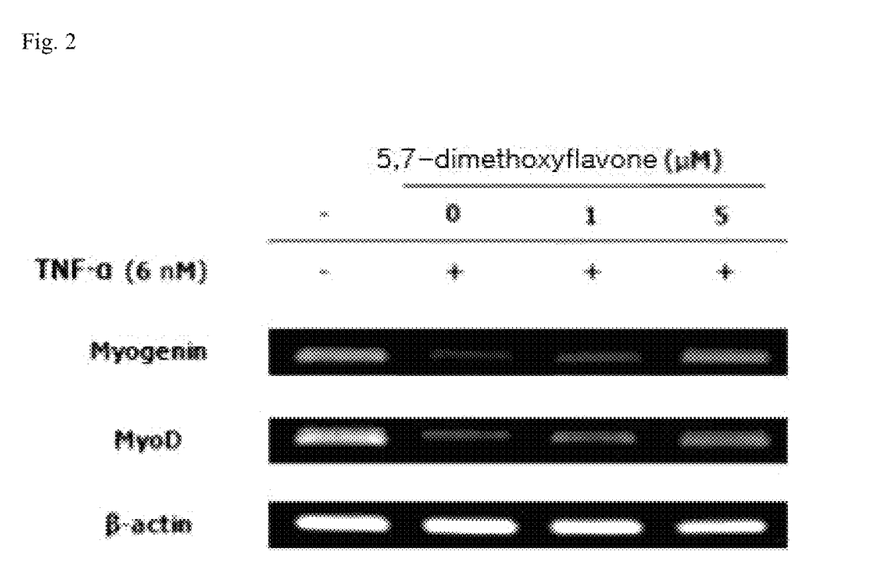
FIG. 2 shows the increased levels of mRNA expression of myogenin and myoD in muscle cells upon application of 5,7-dimethoxyflavone according to the present invention examined by RT-PCR experiments.
Figure 4:
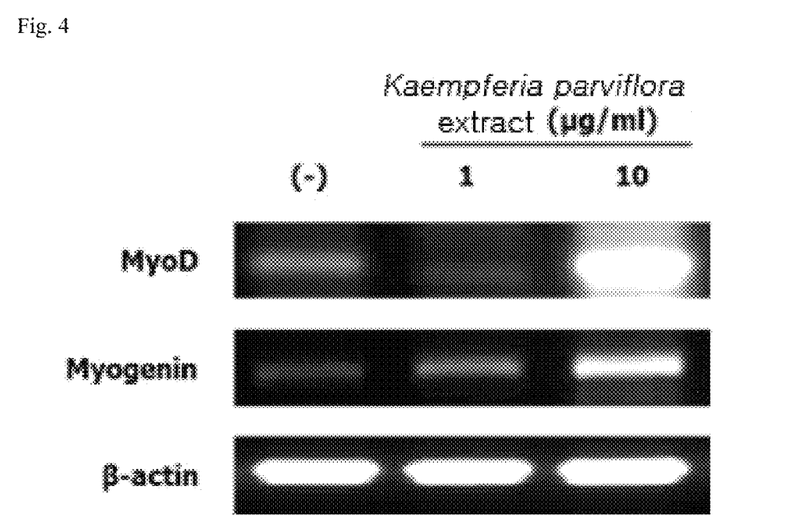
FIG. 4 shows the effect of the extract of *Kaempferia parviflora* in increasing the mRNA levels of muscle differentiation factors, myogenin and myoD in muscle cells.

Relative levels of mRNA for each gene was normalized by the value of β-actin. As shown in FIG. 2, 5,7-dimethoxyflavone increases the mRNA levels of myogenin and myoD, muscle differentiation factors at the level of gene transcription. Furthermore, it was found that the extract of *Kaempferia parviflora* increases the mRNA levels of myogenin and myoD as shown by FIG. 4.

<2-2> Effects of Increasing Protein Anabolism in Muscle Cells

L6 cells were treated in the same manner as Experimental example 1, and were lysed with RIPA buffered solution containing a proteinase inhibitor cocktail. After boiling samples for 5 minutes, same amount of proteins (20 μg) was loaded from each sample and separated in 10% SDS-PAGE gels by electrophoresis. Proteins separated by electrophoresis were transferred onto the nitrocellulose membranes and western blot experiments were performed. Membranes reacted with primary antibodies were rinsed in TBST three times, each for 10 minutes. Primary antibodies used in the present invention were diluted at the ratio of 1:1000. Secondary antibodies (anti-rabbit horseradish) were added to the membranes reacted with primary antibodies and incubated for two hours at room temperature. Secondary antibodies were diluted at the ratio of 1:5000. Protein bands were visualized using ECL western blotting detected reagents (Amersham, Tokyo, Japan). Protein levels of PI3K, p-Akt, and p-mTOR involved in the protein anabolism in the muscles were observed, and the α-tubulin level was used to confirm the consistent loading of proteins across the samples. Experiments using the extract of *Kaempferia parviflora* (1 or 10 μg/ml) were performed in addition to 5,7-dimethoxyflavone. Results from the 5,7-dimethoxyflavone treatment are shown in FIG. 3, and the extract of *Kaempferia parviflora* in FIG. 5.

Figure 3:
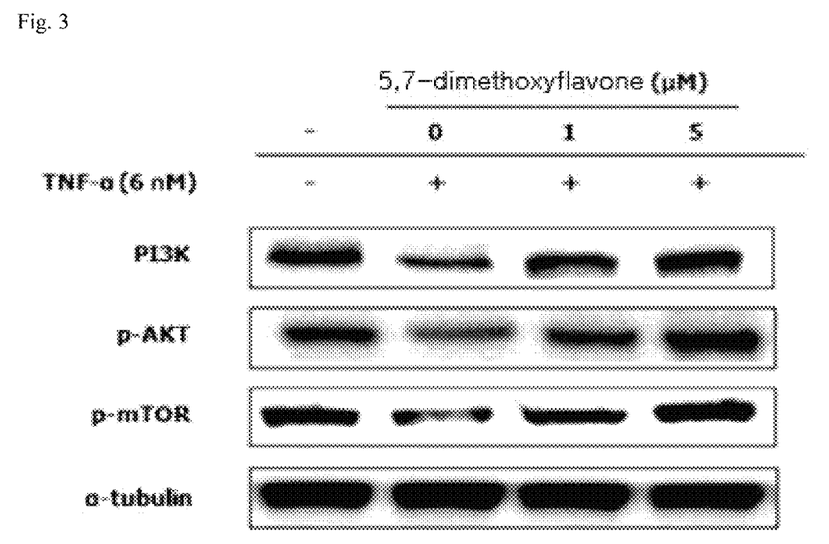
FIG. 3 shows the increased levels of PI3K, p-Akt and p-mTOR proteins in muscle cells upon application of 5,7-dimethoxyflavone according to the present invention examined by western blot experiments.
Figure 5:
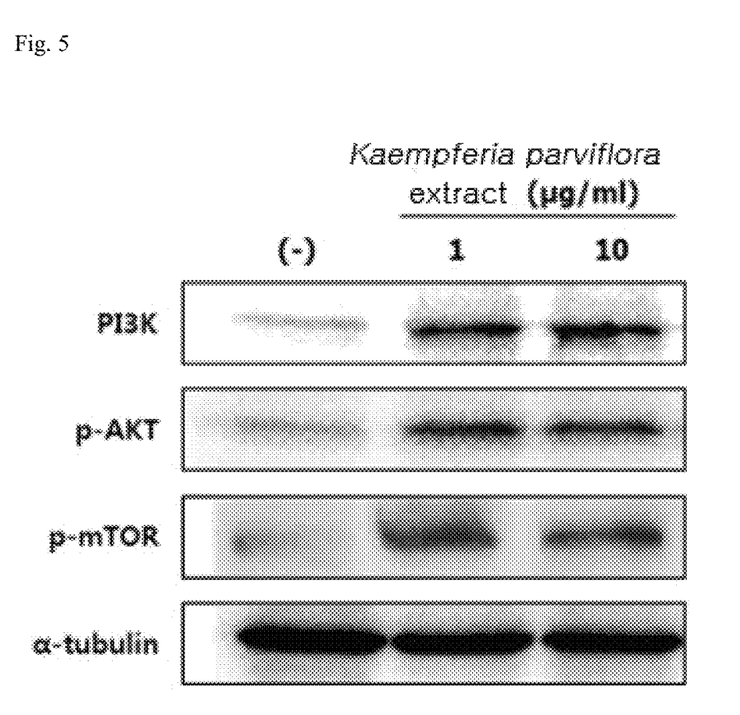
FIG. 5 shows the effect of the extract of *Kaempferia parviflora* in increasing the protein levels of PI3K, p-AKT, and p-mTOR involved in protein synthesis in muscle cells.

As shown in FIG. 3 and FIG. 5, it was confirmed that 5,7-dimethoxyflavone and the *Kaempferia parviflora* extract upregulate the protein levels of PI3K, p-AKT, and p-mTOR. These results suggest that substances of the treatments increase muscle mass and enhance exercise performance.

Experimental Example 3

Effects of Increasing Muscle Mass in the Animal Model

Five-week-old Wistar rats were acclimated for one week and myatrophy was induced by supplying TNF-α at the dose of 100 ng/g for two weeks. Afterwards, rats were randomly divided according to body weight into a total of 4 groups, each consisting of 8 rats. Each of the *Kaempferia parviflora* extract and flavone compounds was suspended in 0.25% carboxymethylcellulose and administered once daily for eight weeks at the dose of 500 mg/kg body weight for the *Kaempferia parviflora* extract, 300 mg/kg body weight for each of 5,7-dimethoxyflavone, 5,7,4'-trimethoxyflavone and 3,5,7,3',4'-pentamethoxyflavone. The control group was administered with the same amount of 0.25% carboxymethylcellulose only as well as TNF-α.

After eight weeks of treatments, calf muscles were dissected out and weighed using microbalance (Mettler PE160, USA). As a result, muscle weights of the animals treated with each of the *Kaempferia parviflora* extract, 5,7-dimethoxyflavone, 5,7,4'-trimethoxyflavone, and 3,5,7,3',4'-pentamethoxyflavone showed increases of 125%, 126%, 118%, and 120% respectively, compared to the control levels with statistical significance (p<0.01). These results suggest that the extract of *Kaempferia parviflora* and flavone compounds isolated from the extract function effectively in increasing muscle mass.

TABLE 1

| Treatment substance | Calf muscle weight (mg) |
| --- | --- |
| TNF-α | 437 |
| *Kaempferia Parviflora* extract | 547 |
| 5,7-dimethoxyflavone | 551 |
| 5,7,4'-trimethoxyflavone | 519 |
| 3,5,7,3',4'-pentamethoxyflavone | 528 |

INDUSTRIAL APPLICABILITY

The extract of *Kaempferia parviflora* and flavone compounds isolated from the extract of the present invention can be useful in preparing a pharmaceutical composition for treating muscle diseases or a dietary composition for improving muscle function because of their effect in reducing protein degradation in the muscles and promoting muscle cell differentiation as well as protein synthesis. Therefore, the present invention is highly applicable in the related industry.

The invention claimed is:

1. A method for increasing muscle mass in a human in need of increasing muscle mass comprising administering a therapeutically effective amount of an ethanol extract of *Kaempferia parviflora* to the human in need of increasing muscle mass wherein said human in need of increasing muscle mass has a muscle disease selected from the group consisting of atony, muscular atrophy, muscular dystrophy, muscle degeneration, myasthenia and sarcopenia.

2. The method of claim 1, wherein the ethanol extract of *Kaempferia parviflora* comprises a compound represented by Formula 4 or a salt thereof:

Formula 4 and wherein each of R1, R2 and R3 is, independently selected from the group consisting of hydrogen and methoxy.

* * * * *